United States Patent [19]

Hartog et al.

[11] Patent Number: 5,424,313
[45] Date of Patent: Jun. 13, 1995

[54] BIBYCLIC HETEROACRYLPIPERAZINE DERIVATIVES HAVING PSYCHOTROPIC ACTIVITY, AND PHARMACEUTICAL COMPOSITIONS CONTAINING THESE DERIVATIVES

[75] Inventors: Jan Hartog; Berend Olivier; Ineke Van Wijngaarden; Cornelis G. Kruse; Johannes A. M. Van Der Heyden; Dirkje A. Van Dalen-Van Der AA, all of Weesp, Netherlands

[73] Assignee: Duphar International Research B.V., Weesp, Netherlands

[21] Appl. No.: 135,189

[22] Filed: Oct. 12, 1993

Related U.S. Application Data

[63] Continuation of Ser. No. 3,683, Jan. 13, 1993, abandoned, which is a continuation of Ser. No. 802,715, Dec. 6, 1991, abandoned, which is a continuation of Ser. No. 593,280, Oct. 5, 1990, abandoned, which is a continuation of Ser. No. 471,694, Jan. 26, 1990, abandoned, which is a continuation of Ser. No. 268,886, Nov. 8, 1988, abandoned, which is a continuation of Ser. No. 161,240, Feb. 18, 1988, abandoned, which is a continuation of Ser. No. 810,094, Dec. 18, 1985, abandoned.

[30] Foreign Application Priority Data

Dec. 21, 1984 [NL] Netherlands ............... 8403917

[51] Int. Cl.$^6$ .............. C07D 241/04; A61K 31/50
[52] U.S. Cl. ............... 514/254; 544/60; 544/121; 544/353; 544/363; 544/368; 544/369; 544/373; 544/376; 544/377; 514/224.2; 514/230.5
[58] Field of Search ............. 544/60, 121, 353, 363, 544/368, 369, 373, 376, 377; 514/225, 227, 254, 224.2, 230.5

[56] References Cited

U.S. PATENT DOCUMENTS 2,976,290  3/1961  Parcell ................... 544/405
4,091,101  5/1978  Lumma, Jr. et al. .......... 544/237

FOREIGN PATENT DOCUMENTS 0138280  4/1985  European Pat. Off. .
2496662  6/1982  France .
2086896  5/1982  United Kingdom .
2097790  11/1982  United Kingdom .

OTHER PUBLICATIONS

Cohen, "Chemical Abstracts", vol. 103, 1985, Col. 103:48166f.
Hartog, et al. "Chemical Abstracts", vol. 103, 1985, Col. 103:123520x.
Cervena, et al., "Chemical Abstracts", vol. 84, 1976, Col. 84:17275a.
Protiva, et al., "Chemical Abstracts", vol. 90; 1979, Col. 90:72223f.
Yang, et al., "Chemical Abstracts", vol. 97, 1982, Col. 97:72386f.
Guerret, et al., "Chemical Abstracts", vol. 98, 1983, Col. 98:10320e.
"Chemical Abstracts", vol. 99, 1983, Col. 99:88225e.
"Chemical Abstracts", vol. 99, 1983, Col. 99:93742a, and 99:122327b.
"Chemical Abstracts", vol. 99; 1983, Col. 99:158276y.
"Chemical Abstracts", vol. 100, 1984, Col. 100:428d.
Cerkovnikov, Prelog, Nov. 10, 1941, pp. 1661–1663.
J. Med. Chem. S., 1965, pp. 104–107 (Ratouis et al).

(List continue on next page.)

Primary Examiner—C. Warren Ivy
Assistant Examiner—Zinna N. Davis
Attorney, Agent, or Firm—Stevens, Davis, Miller & Mosher

[57]  ABSTRACT

The invention relates to new compositions with pyschotropic activity which comprise a compound of formula 1 of the formula sheet as the active substance. The compounds of formula 1 are for the greater part new compounds. The invention therefore also relates to these new compounds and to the preparation thereof in a manner known for the synthesis of analogous compounds.

7 Claims, No Drawings

OTHER PUBLICATIONS

J. Chem. Soc., (C), 1971, pp. 3994–3999, Haddock et al "1,2-3-Benzothiadiazoles. Part V. The Rearrangement . . .".

American Chemical Soc., 1978, p. 275 (Beak et al) "Dipole-Stabilized Carbanions: Novel and Useful Intermediates".

Brit. J. Pharmacol, 1954, pp. 280–284 (Bianchi et al) "Experimental Observations on Haffner's Method for Testing . . .".

Thrombosis Research 18, pp. 189–203 (Kumada et al), 1976 "Experimental Model of Venous Thrombosis in Rats and Effects . . .".

Cerkovnikov, Prelog. pp. 1661–1663.

J. Med. Chem S, 1965, pp. 104–107.

J. Chem. Soc., (C), 1971, pp. 3994–3999.

American Chemical Soc., 1978 p. 275.

Brit. J. Pharmacol 1954, pp. 280–284.

Thrombosis Research 18; pp. 189–203.

Collection of the Czechoslov. Chemical Communications, vol. 40 No. 5, May 1975, pp. 1612–1622, Cervina et al, "Naphthylpipera . . .".

BIBYCLIC HETEROACRYLPIPERAZINE DERIVATIVES HAVING PSYCHOTROPIC ACTIVITY, AND PHARMACEUTICAL COMPOSITIONS CONTAINING THESE DERIVATIVES

This application is a continuation of application Ser. No. 08/003,683, filed Jan. 13, 1993, which in turn is a continuation of application Ser. No. 07/802,715, filed Dec. 6, 1991, now abandoned, which in turn is a continuation of application Ser. No. 07/593,280, filed Oct. 5, 1990, now abandoned, which in turn is a continuation of application Ser. No. 07/471,694, filed Jan. 26, 1990, now abandoned, which in turn is a continuation of application Ser. No. 07/268,886, filed Nov. 8, 1988, now abandoned, which in turn is a continuation of application Ser. No. 07/161,240, filed Feb. 18, 1988, now abandoned, which in turn is a continuation of application Ser. No. 06/810,094, filed Dec. 18, 1985, now abandoned.

The invention relates to new pharmaceutical compositions having a psychotropic activity, to new piperazine derivatives which may be used in such compositions as the active substance, and to the preparation of the said compositions and active compounds.

It was found that compounds of the general formula 1

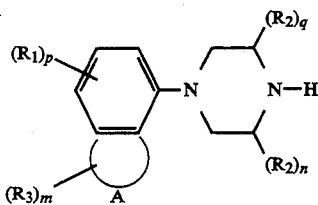

wherein

—$R_1$ is alkyl, cycloalkyl, optionally esterified hydroxyalkyl, alkoxyalkyl, optionally substituted phenyl or heteroaryl, alkoxy, aryloxy, alkylthio, arylthio, alkyl-, alkoxy-, amino-, mono-or dialkylaminocarbonyl, nitro, amino, mono- or dialkylamino, arylamino, cyano, halogen, trifluoromethyl, trifluoromethoxy, optionally esterified hydroxyl, alkyl- or aminosulphonyl or -sulphinyl, mono- or dialkylaminosulphonyl or -sulphinyl, and p has the value 0–3;

—$R_2$ is an alkyl group and n and q can have the value 0 or 1;

—$R_3$ may have the same meaning as $R_1$, or is alkylidene, an oxo or thioxogroup, and m has the value 0–2;

—A forms, with the two carbon atoms of the phenyl group, an optionally entirely or partly unsaturated cyclic group having 5–7 atoms in the ring, which comprises 1–3 hetero atoms from the group O, S and N, with the proviso that the sum of the number of oxygen and sulphur atoms is at most 2, and the acid addition salts of these compounds have interesting psychotropic properties.

As a halogen atom, $R_1$ is preferably fluoro, chloro or bromo, and as an alkyl group, for example, a straight or branched, saturated or unsaturated group having 1–5 carbon atoms.

When $R_2$ is an alkyl group, this is preferably the methyl group or ethyl group.

As a hydroxyalkyl group, the group $R_3$ preferably comprises 1–3 carbon atoms.

When $R_1$ or $R_3$ is an esterified hydroxyl group or hydroxylalkyl group, the ester group preferably has the formula

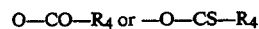

in which $R_4$ is alkyl, aralkyl, aryl, heteroaryl, hetero aralkyl, and alkyl may be branched or unbranched, and the (hetero) aryl part may optionally be substituted, or $R_4$ may be an alkoxy, heteroalkoxy or dialkylamino group, in which the two alkyl groups can form a heterocyclic ring with the nitrogen atom.

When $R_1$ or $R_3$ is an etherified hydroxyl group or hydroxyalkyl group, the ether group preferably has the formula —O—$R_5$, wherein $R_5$ is a straigth, branched or cyclic alkyl group having 1–5 C-atoms, or an alkoxyalkyl group having 1 or 2 C-atoms in both the alkoxy part and in the alkyl part thereof.

Compounds which are preferred on the basis of their activity pattern are:

a) 1-[5-(1,4-benzodioxanyl)]piperazine,
b) 1-[8-(1,3-benzodioxanyl)]piperazine,
c) 1-[7-(benzofuranyl)]piperazine,
d) 1-[4-(1,3-benzodioxolyl)]piperazine,
e) 1-[5-(2-methoxymethyl-1,4-benzodioxanyl)]piperazine,
f) 1-[7-(5-fluorobenzofuranyl)]piperazine,
g) 1-[8-(1,2,3,4-tetrahydroquinolyl)]piperazine,
h) 1-[8-(2-oxo-1-benzopyranyl)]piperazine,
i) 1-[8-(2H-1-benzopyranyl)]piperazine,
j) 1-[5-(2-methyl-1,4-benzodioxanyl)]piperazine,
k) 1-[7-(4-fluorobenzofuranyl)]piperazine,
l) 1-[8-(isoquinolyl)]piperazine,
m) 1-[7-(4-bromobenzofuranyl)]piperazine,
n) (+)-1-[5-(2-methoxymethyl-1,4-benzodioxanyl)]piperazine,
o) 1-[7-(4-methylbenzofuranyl)]piperazine,
p) 1-[7-(4-chlorobenzofuranyl)]piperazine,
q) 1-[7-(5-chlorobenzofuranyl)]piperazine.

The so-called prodrugs of the compounds of formula 1, i.e. derivatives of the compounds of the formula 1 which are inactive as such and which after administration are converted in the body into active compounds of formula 1 also belong to the invention.

When a chiral carbon atom is present, both the racemate and the individual isomers belong to the invention.

Suitable acids with which the compounds of formula 1 can form pharmaceutically acceptable acid additon salts are, for example, hydrochloric acid, sulphuric acid, phosphoric aced, nitric acid, and organic acids such as citric acid, fumaric acid, maleic acid, tartaric acid, acetic acid, benzoic acid, p-toluenesulphonic acid, methanesulphonic acid, and naphtalenesulphonic acid.

The above-described compounds of formula 1 have a psychotropic activity and are hence excellently suitable for the treatment of affections or diseases which are the result of disturbances in the central nervous system, for example, psychoses, aggression, fear, depression, etc. Some of the compounds moreover have also a good central analgetic activity.

Dependent on the meanings of the symbols A, $R_1$–$R_3$, m, n, p and q some compounds of the formula 1 have a strong thrombolytic activity. This property makes these compounds particularly suitable for use in the treatment of hematological disorders.

An important advantage of the present compounds of formula 1 is that their activity is very specific. It was found, for example, that in mice the antiaggressive activity is not associated with undesired sedative effects.

As a rule the antipsychotic activity is produced without the side effects, which are generally considered to be undesired, as a result of dopaminolytic and sedative activity.

Dependent on the meanings of the groups A and $R_1$-$R_3$, both the antiaggressive activity and the antipsychotic activity may be most prominent.

The antiaggressive activity of the compounds was measured in a test suitable for that purpose on isolated mice (Advances in Pharmacol. 5, (1967), 79). In this test, male albino mice were kept isolated for a period of 4 weeks and were then selected for the test on the basis of fighting behaviour present. The selection criterion is the occurrence of 3 or more fighting periods within 3 minutes after a mouse which had not been kept isolated is placed in the cage of the mouse which had been kept isolated.

The compounds to be investigated were administered orally to the selected mice. Five mice per dose were used. Sixty minutes after administration of the compound to be investigated, the animals were again evaluated for fighting behaviour. The compound to be investigated is inactive in the administered dose when in this case also 3 or more fighting periods were observed within 3 minutes after a mouse which had not been kept isolated was placed in the cage of the mouse which had been kept isolated. The $ED_{50}$-value in mg of active substance per kg of body weight was calculated form the results obtained.

The compounds according to the invention have an $ED_{50}$-value which is smaller than 20 mg/kg and for most of the compounds the $ED_{50}$-value is 0.1-5 mg/kg.

Due to the strong antiaggressive activity and the absence of undesired side effects, for example, sympatholytic, dopaminolytic, muscle relaxing and sedative properties, the compounds are excellently suitable for use in the treatment of intra- and extrapunitive behaviour and overt aggressive behaviour in man and animal.

For use in humane medicine are to be considered first of all the control of aggressive symptoms in psychiatric diseases and serious forms of psychopathological aggression.

As application possibilities in the veterinary field are to be considered especially those forms of aggression which occur in the transport of agricultural domestic animals and the mixing of groups of these animals.

The antipsychotic activity of the compounds of formula 1 was determined in a test procedure in which the suppression of conditioned behaviour in test animals was measured according to procedures known per se. The compounds are considered to be active if they show at least a suppression of 50% of the conditioned behaviour after oral administration in dosages of 50 mg/kg or less. The dopaminolytic activity of these compounds can be determined according to known behavioural or biochemical tests, for example, induction of catalepsy, increasing of the dopamine synthesis or conversion rate in the central nervous system, and by the affinity to dopamine receptors which is determined by displacement of a radioactive labelled ligand in a tissue homogenate.

The sedative activity of these compounds was studied in a test in which the influencing of the spontaneous locomotoric activity of test animals is measured according to known methods.

For the active compounds of formula 1 it was found that generally dopaminolytic and sedative effects do not occur in dosages which are at least a factor three higher than the dosages which give 50% suppression of the conditioned behaviour.

The quantity, frequency and way of administration may differ for each individual case, also dependent on the nature and the severity of the disturbances. A dosage of 5-500 mg and preferably of 25-150 mg daily are generally suitable for humane application.

For veterinary purposes the dosage preferably is 0.1-10 mg/kg of body weight.

The analgetic activity of the compounds was determined in an analgetic test in mice (Brit. J. Pharm. 9, (1954), 280). In this test the pain stimulus was generated by placing bulldog clips on the tailhead of a mouse. The animals try to remove the pain stimulus by biting. The non-occurence of the pain response after administration of test substances is a measure of the analgetic activity. The compounds to be tested were administered orally. Five mice were used per dose. Sixty minutes after the administration of the compounds to be tested, the occurrence of the pain response was established. From the results obtained the $ED_{50}$-values in mg/kg of active substance per kg of body weight were calculated.

The thrombolytic activity is determined using the method described by Kumada et al (Thrombosis Research, 18, (1980), 189-203).

The active compounds according to the invention and their salts can be processed, according to known standard methods, to compositions such as pills, tablets, coated tablets, capsules, powders, injection liquids, and the like while using the conventional auxiliary substances, for example, solid and liquid carrier materials.

The compounds of formula 1 are new compounds with the exception of the compounds wherein n and q are 0, and A together with the two carbon atoms of the phenyl group forms a heterocyclic group having 5 or 6 ringatoms, which as the only hetero atom contains one nitrogen atom at the meta position in relation to the piperazine group (some of these compounds are known from French patent specification 81.23744), and compounds in which n and q are 0, and the group of formula 2

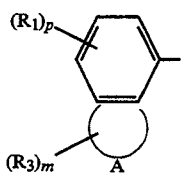

(2)

is a 4-(or 7-)benzimidazolyl group which may be substituted in position 2 with alkyl or phenyl, or a 7-indolyl group, or a 4-(or 7-)benzotriazolyl group (which compounds are known from Netherlands Patent Application 82.01708), or a 5-(or 8-)carbo (or 3,4-dihydrocarbo-)styryl group (which compounds are known from Netherlands patent application 81.04923), or an 8-quinolinyl group (which compound is known from Ber. 74B, (1941), pp. 1661-1663).

The new compounds according to the invention can be prepared in a manner known for the synthesis of analogous compounds (see, for example, U.S. Pat. No. 2,976,290 and J. Med. Chem. 8, (1965), pp. 104-107).

The compounds can be obtained, for example, by reaction of a compound of formula 3

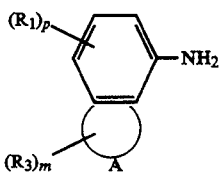 (3)

with a compound of formula 4,

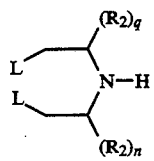 (4)

in which formula L is a so-called leaving group, preferably chlorine, bromine, alkyl-SO₃ or aryl-SO₃.

This reaction may be carried out both in an inert apolar organic solvent, and in a protic polar solvent. Examples of suitable solvents are chlorobenzene, toluene, pyridine, acetonitrile, lower aliphatic alcohols, for example, ethanol, propanol and butanol. In order to bind the releasing acid, an acid binder, for example NaHCO₃ or K₂CO₃ or an organic base, for example, triethylamine, may be used. The reaction temperature usually is between room temperature and the boiling-point of the solvent used.

It is sometimes necessary or desired in this mode of preparation first to replace the hydrogen atom at the nitrogen atom in the starting material of formula 4 by a protective group, for example, the benzyl group, an aryloxycarbonyl group or alkoxycarbonyl group the alkoxy group of which comprises 1-4 C-atoms. Said protective group can then be removed from the resulting final product by means of the methods conventionally used for this purpose, for example, by catalytic hydrogenation or by acid hydrolysis. Conventional solvents are lower aliphatic alcohols and aliphatic esters thereof or aqueous mineral acid. The reactions are carried out at temperatures between room temperature and reflux temperature of the solvent used.

The compounds of formula 1 can furthermore be obtained by reduction of a compound of formula 5

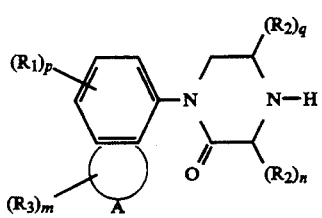 (5)

or formula 6,

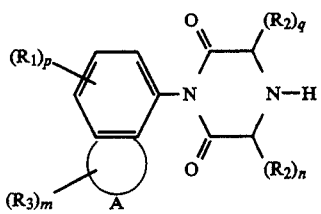 (6)

in which the symbols have the above-mentioned meanings. This reduction reaction may be carried out, for example, with suitable reduction agents, for example LiAlH₄ or a BH₃.S(CH₃)₂-complex in a suitable solvent, for example, ether or tetrahydrofuran. The reaction is carried out at temperatures between room temperature and the reflux temperature of the solvent used. This method can be used readily only when besides the keto group or keto groups to be reduced, no other groups sensitive to reduction are present in the starting substances of formula 5 or 6.

Another suitable method of preparing the compounds of formula 1 is the reaction of a compound of formula 7

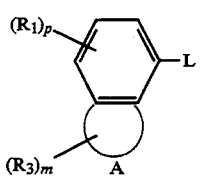 (7)

with a piperazine of formula 8,

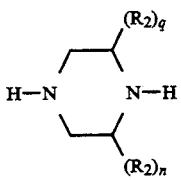 (8)

in which A, R₁-R₃, p, n, q and m have the above-mentioned meanings and L is a leaving group, for example, a halogen atom or nitro group. This reaction is carried out in a suitable organic solvent, for example, toluene, xylene, or a mono- or polyalcohol of higher boiling-point, at the reflux temperature of the solvent used.

The compounds of formula 1 can further be prepared by reaction of a compound of formula 9

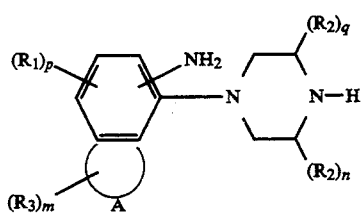 (9)

with NaNO₂ in the manner described, inter alia, in J. Chem. Soc. 1971, 3994-3999 in a sulphuric acid or hydrochloric acid medium, in which the resulting diazonium salt is decomposed with, for example, 50% hypophosphoric acid. The reaction is carried out at temperatures between 0° C. and room temperature.

Some compounds of formula 1 can furthermore be obtained by conversion of another compound of formula 1. For example, compounds of formula 1, in which $R_1$ and/or $R_3$ is/are an esterified hydroxyl function, can be converted by hydrolysis via a method known per se into compounds in which $R_1$ and/or $R_3$ is/are hydroxyl. The reverse is also possible. Another possibility is to saturate or introduce a double bond in compounds of formula 1, by hydrogenation or dehydrogenation, dependent on the structure.

Moreover, compounds of the formula 1, wherein n and/or q has the value 1 can be obtained by introducing one or two groups $R_2$ starting with the corresponding compounds of the formula 1 wherein n and/or q has the value 0. According to this process (Chem. Rev. 78, (1978), 275 and 84, (1984), 471) a compound of the formula 1 is converted into a compound of the formula 10

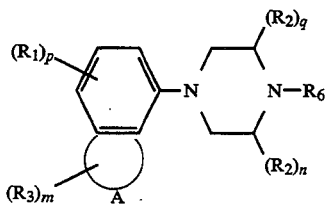

wherein $R_1$-$R_3$, m, n, p and q have the above meanings, and $R_6$ is an activating group, for example a nitroso group. Then the compound of formula 10 is alkylated with a compound $R_2$-L, wherein $R_2$ and L have the above meanings. After the alkylation the activating group $R_6$ is removed in a way known per se, whereby the desired compound of formula 1 is obtained.

The reaction is carried out in a suitable organic solvent such as for example a lower alkane, diethyl ether or tetrahydrofuran, in the presence of a strong base, for example aryl- or alkyllithium or a lithium dialkylamine, at temperatures preferably between $-100°$ C. and $0°$ C.

Finally, compounds of formula 1 can be obtained, dependent on the meaning of A, by converting compounds of formula 11

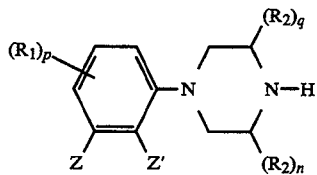

into compounds of formula 1 by a cyclisation reaction. This cyclisation generally takes place, dependent on the meanings of Z and Z' and the desired meaning of A, via methods known per se for this type of substances or analogous thereto.

The starting materials to be used in the above-described methods can be obtained, in so far as these are new compounds, in a manner known for the synthesis of analogous compounds.

The invention will be further described with reference to the ensuing specific examples.

EXAMPLE I

1-[5-(1,4-benzodioxanyl)]piperazine, hydrochloride.

128 Mmol (23.9 g) of 5-amino-1,4-benzodioxan and 140 mmol (25.0 g) of bis-(2-chloroethyl)amine HCL were suspended in 250 ml of chlorobenzene. The mixture was heated at $130°$ C. for 66 hours while stirring. The reaction mixture was cooled to $90°$ C. and diluted with 200 ml of ethyl acetate. The solid was filtered off and washed with ethyl acetate. The crude substance was recrystallized from ethanol and the title compound was obtained having a melting-point of $256°$-$258°$ C.

EXAMPLE II

1-[8-(1,3-benzodioxanyl)]piperazine, hydrochloride.

18.7 Mmol (5.8 g) of 1-[8-(1,3-benzodioxanyl)]-4-benzylpiperazine were dissolved in 150 ml of 96% ethanol after which 1 g of 10% palladium on carbon was added. The mixture was then hydrated at $50°$ C. with 450 ml of hydrogen. The reaction mixture was filtered over hyflo and the filtrate was evaporated to dryness under reduced pressure. The evaporation residue was dissolved in 100% ethanol and 1 equivalent of hydrochloric acid in ethanol was added hereto. The solution was treated with carbon and after filtration over hyflo the filtrate was diluted with ether. The title compound was isolated with a melting-point of $217°$-$219°$ C.

EXAMPLE III

1-[5-(1,4-benzodioxanyl)]-3-methylpiperazine, hydrochloride.

64 Mmol (16,7 g) of 1-[5-(1,4-benzodioxanyl)]-3-methylpiperazine-2,6-dione were dissolved under an atmosphere of nitrogen in 200 ml of tetrahydrofuran distilled over lithium aluminium hydride. 170 Mmol (12.9 g) of borane-dimethyl sulphide complex (16.3 ml) were carefully added to this solution, after which the whole was heated slowly to $40°$ C. During the moderately exotherm reaction, a mixture of dimethylsulphide and tetrahydrofuran was distilled off, the total volume of the reaction mixture being kept constant by simultaneously adding dropwise tetrahydrofuran. After 300 ml of distillate had been collected, the reaction mixture, in which a precipitate had formed, was cooled to $-10°$ C. At this temperature, 80 ml of 6N hydrochloric acid were added dropwise, after which the reaction mixture, without a cooling bath, slowly reached room temperature. After leaving to stand for 16 hours, the mixture was heated to reflux in which a bright solution was formed and tetrahydrofuran was distilled off. While cooling with ice, 270 ml of 2N sodium hydroxide were added to this solution, after which the mixture was extracted with $3\times300$ ml of ethyl acetate. The organic layer was washed with water and then dried on sodium sulphate and evaporated to dryness in vacuo. The residue after evaporation was dissolved in a mixture of ethyl acetate-ethanol and 1 equivalent of hydrochloric acid in ethanol was added hereto, after which the title compound was obtained with a melting-point of $220°$-$224°$ C.

EXAMPLE IV 5-(1-piperazinyl)quinoxalin, hydrochloride.

0.2 Mol (33.5 g) of 5-chloroquinoxalin and 2.1 mol (184 g) of piperazine were mixed in 180 ml of ethylene glycol and refluxed for 20 hours.

The reaction mixture was poured on ice and acidified with concentrated hydrochloric acid and then extracted with $3\times200$ ml of ether. The water layer was made alkaline while cooling with ice, with 50% sodium hydroxide and then extracted with $3\times600$ ml of methylene chloride. The combined methylene chloride solution was washed successively with 1 l of 1N sodium hydroxide and a mixture of 925 ml of a saturated saline solution and 75 ml of 50% potassium hydroxide. The organic solution was dried on sodium sulphate and was then evaporated to dryness in vacuo. The residue was chromatographed over silica gel with a mixture of methylene chloride, methanol, and 25% ammonia (92:7.5:0.5) as eluent. The resulting free base was dissolved in ethanol and 1 equivalent of hydrochloric acid in ethanol was added. The title compound was obtained with a melting-point of 271°–272° C.

EXAMPLE V

1-[5-(2-hydroxymethyl-1,4-benzodioxanyl)]piperazine, dihydrochloride.

6,6 Mmol of 1-[5-(2-benzoyloxymethyl-1,4-benzodioxanyl)]piperazine were suspended in 100 ml of ethanol, after which a solution of 0.95 g of 85% KOH in 10 ml of water was added in one portion. After stirring at room temperature for 2.5 hours, the suspension was concentrated by evaporation at reduced pressure. The residue was then extracted with chloroform. The residue obtained after evaporation was finally converted with 2 equivalents of hydrochloric acid into the dihydrochloride of the title compound with a melting-point of 228°–233° C.

EXAMPLE VI

1-[8-(1,2,3,4-tetrahydroquinolinyl)]piperzine, dihydrochloride.

7.5 g Of $NiCl_2.6H_2O$ were added while stirring at 10°–15° C. to 10.5 mmol of 1-(8-quinolinyl) piperazine in 75 ml of methanol. 11.9 g Of $NaBH_4$ were then added in portions in approximately 30 hours at 10°–20° C. The reaction mixture was worked up by pouring in a mixture of 70 ml of water and 30 ml of concentrated hydrochloric acid. After heating at 90° C. for 20 minutes, the mixture was cooled and 20 ml of 50% NaOH solution was added. The title compound was finally obtained by extraction with chloroform and a chromatographic purification over silica gel, succeeded by the preparation of the dihydrochloride with 2 equivalents of hydrochloric acid in ethanol. Melting-point 330°–334° C.

EXAMPLE VII

1-[4-(3-methyl-1,2-benzisoxazoayl)]piperazine fumarate.

86.9 Mmol of 1-(3-fluoro-2-acetyloxim-phenyl) piperazine were dissolved in 100 ml of DMSO, after which 6.7 g of 85% KOH were added. The mixture was poured in 500 ml of water, while stirring, and extracted with 3×300 ml of ethyl acetate. The product obtained after drying on magnesium sulphate and evaporation was dissolved in hot ethanol, after which 1 equivalent of fumaric acid was added in 150 ml of hot ethanol. The title compound was sucked off after crystallization and had a melting-point of 216°–219° C.

Analogously to the methods described in the Examples I to VII, the compounds of formula 12

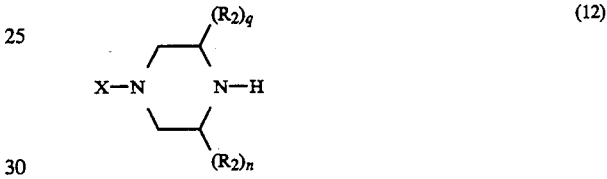

(12)

recorded in the table below were prepared according to the method of-the specific example also mentioned in the table:

TABLE

| Comp. No. | X | $(R_2)_n$ | $(R_2)_q$ | Salt | Melt.-point (°C.) | Method of Ex. |
|---|---|---|---|---|---|---|
| 1 | benzo[1,3]dioxole-4-yl | H | H | HCl | 222–224 | I |
| 2 | 1,4-benzodioxan-5-yl | H | H | HCl | 256–258 | I |
| 3 | 2,3-dihydro-1,4-benzodioxepin-6-yl | H | H | HCl | 266–269 | I |
| 4 | 1,4-benzodioxan-5-yl | Me | H | HCl | 220–224 | III |
| 5 | 2-(hydroxymethyl)-1,4-benzodioxan-5-yl | H | H | 2HCl | 228–233 | V |

TABLE-continued

| Comp. No. | X | $(R_2)_n$ | $(R_2)_q$ | Salt | Melt.-point (°C.) | Method of Ex. |
|---|---|---|---|---|---|---|
| 6 | benzodioxane-C(=O)OH (+) | H | H | 2HCl | 226–230 | V |
| 7 | benzodioxane-C(=O)OH (−) | H | H | 2HCl | 236–240 | V |
| 8 | benzodioxane-C-O-C(=O)-Ph | H | H | HCl | 186–189 | I |
| 9 | benzodioxane-C-O-C | H | H | HCl | 179–181 | I |
| 10 | benzodioxane-C-OH | H | H | HCl | 228–235 | V |
| 11 | benzodioxane-C(-OH)(C) | H | H | FUM. | 125 (decomp.) | V |
| 12 | benzodioxine | H | H | HCl | 217–219 | II |
| 13 | benzodioxine isomer | H | H | HCl | 266 (decomp.) | II |
| 14 | chroman | H | H | HCl | 261–265 | I |
| 15 | benzofuran | H | H | Cl | 190–192 | I |
| 16 | dihydrobenzofuran | H | H | 2HCl | 215–218 | I |

| Comp. No. | X | $(R_2)_n$ | $(R_2)_q$ | Salt | Melt.-point (°C.) | Method of Ex. |
|---|---|---|---|---|---|---|
| 17 | 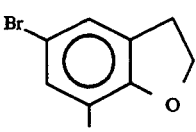 | H | H | HCl | 235–240 | I |
| 18 | 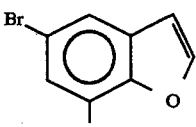 | H | H | HCl | 288–290 | I |
| 19 | 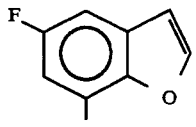 | H | H | 2HCl | 196–199 | I |
| 20 | 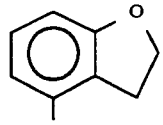 | H | H | HCl | 240–245 | I |
| 21 | 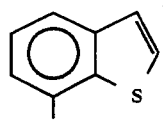 | H | H | HCl | 240 | II |
| 22 | 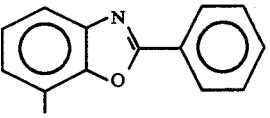 | H | H | 0.5 FUM. | 226–228 | I |
| 23 | 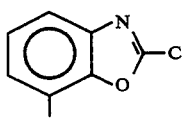 | H | H | FUM. | 195–196 | I |
| 24 | 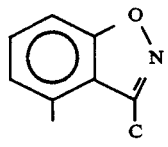 | H | H | FUM. | 216–219 | VII |
| 25 | 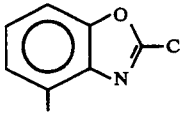 | H | H | — | oil | I |
| 26 | 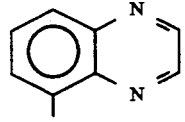 | H | H | HCl | 271–272 | IV |
| 27 | 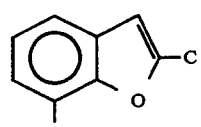 | H | H | 2HCl | 216–222 | I |

TABLE-continued
| Comp. No. | X | $(R_2)_n$ | $(R_2)_q$ | Salt | Melt.-point (°C.) | Method of Ex. |
|---|---|---|---|---|---|---|
| 28 | 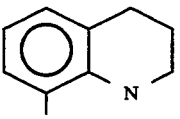 | H | H | 2HCl | 330–334 | VI |
| 29 | 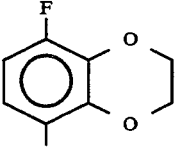 | H | H | 2.HCl | 215–221 | I |
| 30 | 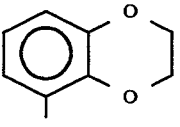 | Me (cis) | Me | HCl | 277–283 | III |
| 31 | 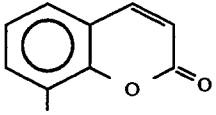 | H | H | HCl | 250 (dec.) | I |
| 32 | 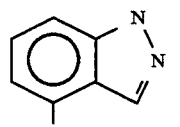 | H | H | maleaat resin | | II |
| 33 | 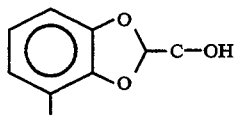 | H | H | 2.HCl | 195–197,5 | II |
| 34 | 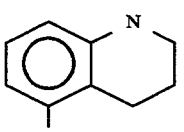 | H | H | 2.HCl | 295–300 | VI |
| 35 | 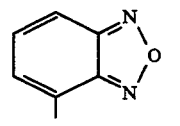 | H | H | HCl | 250 (dec.) | IV |
| 36 | 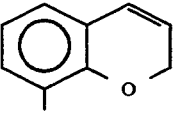 | H | H | 2.HCl | 219–220 | II |
| 37 | 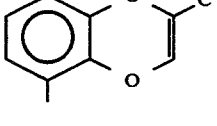 | H | H | FUM. | 208–211 | VI |
| 38 | 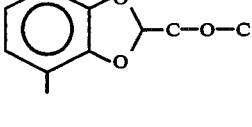 | H | H | 2.HCl | 190–193,5 | II |

TABLE-continued

| Comp. No. | X | $(R_2)_n$ | $(R_2)_q$ | Salt | Melt.-point (°C.) | Method of Ex. |
|---|---|---|---|---|---|---|
| 39 | benzodioxine-CH₂ | H | H | FUM. | 164–166 | II |
| 40 | benzodioxine-C(OH)< | H | H | 2.HCl | 216–218 | II |
| 41 | benzodioxine-CH | H | H | 2.HCl | 240–245 | VI |
| 42 | isoquinoline | H | H | 2.HCl | 280–290 | V |
| 43 | indoline | H | H | 2.HCl | 257,5–265 | VI |
| 44 | benzothiaoxine | H | H | 2.HCl | 276–280 | I |
| 45 | chromanone | H | H | 2.HCl | 207–212 | I |
| 46 | fluoro-benzofuran | H | H | 2.HCl | 224 (dec.) | I |
| 47 | benzodioxepine | H | H | 2.HCl | 280–285 | II |
| 48 | benzodioxine-CH-O-C (+) | H | H | 2.HCl | 195–197 | II |
| 49 | benzodioxine-CH-O-C (−) | H | H | 2.HCl | 196–200 | II |

TABLE-continued

| Comp. No. | X | (R₂)ₙ | (R₂)q | Salt | Melt.-point (°C.) | Method of Ex. |
|---|---|---|---|---|---|---|
| 50 | benzodioxane-CH(OH)-C | H | H | 2.HCl | 263–265 | II |
| 51 | 5-fluoro-1,3-benzodioxole | H | H | HCl | 228–229 | I |
| 52 | indoline | H | H | 2.HCl | 284–288 | VI |
| 53 | benzoxazol-2(3H)-one | H | H | 2.HCl | 300 (dec.) | I |
| 54 | isoquinoline | H | H | 2.HCl | 240 (dec.) | IV |
| 55 | 5-Cl-benzofuran | H | H | HCl | 208–210 | I |
| 56 | 5-Cl-benzofuran | H | H | HCl | 236–240 | I |
| 57 | 4-Br-benzofuran | H | H | HCl | 235,5–236 | VI |
| 58 | 3-Br-benzofuran | H | H | HCl | 228–234 | I |
| 59 | benzoxazole | H | H | resin | | II |
| 60 | 5-Cl-O-benzofuran | H | H | 2.HCl | 186–190 | I |

TABLE-continued
| Comp. No. | X | $(R_2)_n$ | $(R_2)_q$ | Salt | Melt.-point (°C.) | Method of Ex. |
|---|---|---|---|---|---|---|
| 61 | 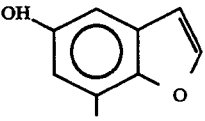 | H | H | free base | 195–198 | VI |
| 62 | 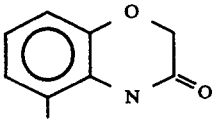 | H | H | HCl | 310–330 | II |
| 63 | 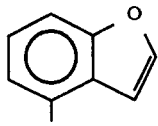 | H | H | HCl | 200–205 | I |
| 64 | 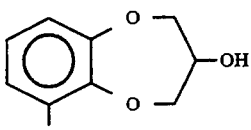 | H | H | 2.HCl | 233 (dec.) | II |
| 65 | 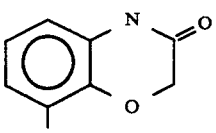 | H | H | HCl | 290 (dec.) | I |
| 66 | 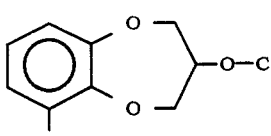 | H | H | 2.HCl | 200–202 | II |
| 67 | 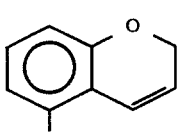 | H | H | HCl | 285–286 | II |
| 68 | 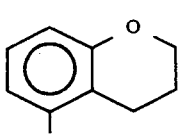 | H | H | HCl | 330–331 | VI |
| 69 | 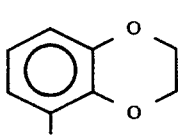 | Me (trans) | Me | HCl | 236–240 | III |
| 70 | 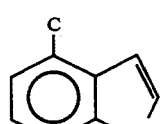 | H | H | HCl | 170–173 | I |
| 71 | 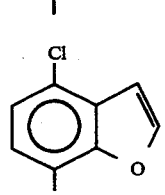 | H | H | HCl | 196–198 | I |

TABLE-continued

| Comp. No. | X | (R₂)ₙ | (R₂)_q | Salt | Melt.-point (°C.) | Method of Ex. |
|---|---|---|---|---|---|---|
| 72 | 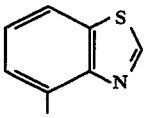 | H | H | HCl | 256–258 | I |

We claim:

1. A pharmaceutical composition which comprises a psychotropically effective mount of at least one piperazine derivative of formula I,

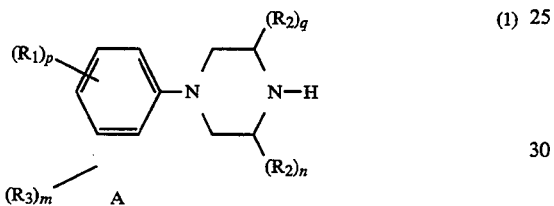

in which

— $R_1$ is alkyl having 1–5 C-atoms, cycloalkyl having 3–7 atoms, alkoxy or alkylthio having 1–5 C-atoms, nitro, mono- or dialkylamino having 1–5 C-atoms in the alkyl group, cyano, trifluoromethyl, trifluoromethoxy, hydroxy, alkylcarbonyloxy having 1–5 C-atoms in the alkyl group, phenylcarbonyloxy or phenyl which is unsubstituted or substituted with halogen or alkyl having 1–3 C-atoms, and p has the value 0–3;

— $R_2$ is alkyl having 1–5 C-atoms and n and q have the value 0 or 1;

— $R_3$ may have the same meanings as $R_1$, or is alkylidine having 1–5 C-atoms, oxo, thioxo, hydroxyallcyl having 1–5 C-atoms, alkoxyalkyl having 1–5 C-atoms, allkylcarbonyloxyalkyl having 1–3 C-atoms in the alkyl groups, phenylcarbonyloxyalkyl having 1–3 C-atoms in the alkyl group, and m has the value 0, 1 or 2; and — A forms, with the two carbon atoms of the phenyl group, an optionally fully or partly unsaturated cyclic group having 5–7 atoms in the ring, which consists of 1–3 hereto atoms from the group O, S and N, the remainder of the atoms in the ring being C-atoms with the proviso that the sum of the number of oxygen and sulfur atoms is at most 2, or a pharmaceutically acceptable acid addition salt or enantiomer thereof; with the provisos that a) when A together with the two carbon atoms of the phenyl group forms a heterocyclic group having 5 or 6 ring atoms only one hetero atom is present and the hetero atom therein cannot be a nitrogen atom on the meta position in relation to the piperazine group if n=0, and b) compounds in which the group of formula 2

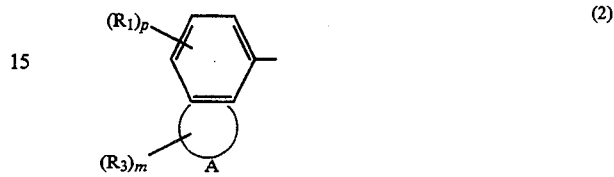

is selected from the group consisting of
4-benzimidazolyl which is unsubstituted or substituted in position 2 with alkyl or phenyl,
7-benzimidazolyl which is unsubstituted or substituted in position 2 with alkyl or phenyl,
7-indolyl,
4-benzotriazolyl,
7-benzotriazolyl,
5-carbo styryl,
8-carbo styryl,
3,4-dihydrocarbo styryl, and
8-quinolinyl are not included; and a carrier material.

2. A composition as claimed in claim 1, wherein the piperazine derivative is present in an amount which is antiagressively effective.

3. A composition as claimed in claim 1, wherein the piperazine derivative is present in an amount which is antipsychotically effective.

4. A method of treating affections or diseases which are the result of disturbances in the central nervous system of a patient, comprising administering a psychotropically effective mount of a pharmaceutical composition which comprises a psychotropically effective mount of at least one piperazine derivative of formula I, in which — $R_1$ is alkyl having 1–5 C-atoms, cycloalkyl having 3–7 atoms, alkoxy or alkylthio having 1–5 C-atoms, nitro, mono- or dialkylamino having 1–5 C-atoms in the alkyl group, cyano, trifluoromethyl, trifluoromethoxy, hydroxy, alkylcarbonyloxy having 1–5 C-atoms in the alkyl group, phenylcarbonyloxy or phenyl which is unsubstituted or substituted with halogen or alkyl having 1–3 C-atoms, and p has the value 0–3;

— $R_2$ is alkyl having 1–5 C-atoms and n and q have the value 0 or 1;

— $R_3$ may have the same meanings as $R_1$, or is alkylidine having 1–5 C-atoms, oxo, thioxo, hydroxyallcyl having 1–5 C-atoms, alkoxyalkyl having 1–5 C-atoms, allkylcarbonyloxyalkyl having 1–3 C-atoms in the alkyl groups, phenylcarbonyloxyalkyl having 1–3 C-atoms in the alkyl group, and m has the value 0, 1 or 2; and — A forms, with the two carbon atoms of the phenyl group, an optionally fully or partly unsaturated cyclic group having 5–7 atoms in the ring, which consists of 1–3 hetero atoms from the group O, S and N, the remainder of the atoms in the ring being C-atoms with the proviso that the sum of the number of oxygen and sulfur atoms is at most 2, or a pharmaceutically acceptable acid addition salt or enantiomer thereof; and a carrier material to the patient.

5. A piperazine derivative of formula I

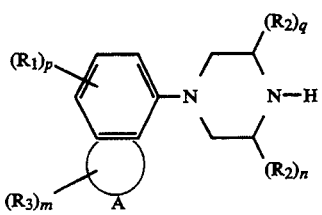

in which

— $R_1$ is alkyl having 1–5 C-atoms, cycloalkyl having 3–7 C-atoms, alkoxy or alkylthio having 1–5 C-atoms, nitro, mono- or dialkylamino having 1–5 C-atoms in the alkyl group, cyano, trifluoromethyl, trifluoromethoxy, hydroxy, alkylcarbonyloxy having 1–5 C-atoms in the alkyl group, phenylcarbonyloxy or phenyl which is unsubstituted or substituted with halogen or alkyl having 1–3 C-atoms, and p has the value of 0–3;

— $R_2$ is alkyl having 1–5 C-atoms and n and q have the value 0 or 1;

— $R_3$ may have the same meanings as $R_1$, or is alkylidine having 1–5 C-atoms, oxo, thioxo, hydroxylalkyl having 1–5 C-atoms, alkoxyalkyl having 1–5 C-atoms, alkylcarbonyloxyalkyl having 1–3 C-atoms in the alkyl groups, phenylcarbonyloxyalkyl having 1–3 C-atoms in the alkyl group, and m has the value 0, 1 or 2; and — A forms, with the two carbon atoms of the phenyl group, an optionally fully or partly unsaturated cyclic group having 5–7 atoms in the ring, which consists of 1–3 hetero atoms from the group O, S and N, the remainder of the atoms in the ring being C-atoms with the proviso that the sum of the number of oxygen and sulphur atoms is at most 2, or a pharmaceutically acceptable acid addition salt or enantiomer thereof, with the provisos that a) when A together with the two carbon atoms of the phenyl group forms a heterocyclic group having 5 or 6 ring atoms only one hetero atom is present and the hetero atom therein cannot be a nitrogen atom on the meta position in relation to the piperazine group if n=0, and b) compounds in which the group of formula 2

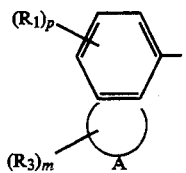

is selected from the group consisting of
4-benzimidazolyl which is unsubstituted or substituted in position 2 with alkyl or phenyl,
7-benzimidazolyl which is unsubstituted or substituted in position 2 with alkyl or phenyl
7-indoyl,
4-benzotriazolyl,
7-benzotriazolyl,
5-carbo styryl,
8-carbo styryl,
3,4-dihydrocarbo styryl, and
8-quinolinyl are not included.

6. A composition as claimed in claim 1, wherein the piperazine derivative is selected from the group consisting of
a) 1-[5-(1,4-benzodioxanyl)]piperazine,
b) 1-[8-(1,3-benzodioxanyl)]piperazine,
c) 1-[7-(benzofuranyl)]piperazine,
d) 1-[4-(1,3-benzodioxolyl)]piperazine,
e) 1-[5-(2-methoxymethyl-1,4-benzodioxanyl)]piperazine,
f) 1-[7-(5-fluorobenzofuranyl)]piperazine,
g) 1-[8-(1,2,3,4-tetrahydroquinolyl)]piperazine,
h) 1-[8-(2-oxo-1-benzopyranyl)]piperazine,
i) 1-[8-(2H-1-benzopyranyl)]piperazine,
j) 1-[5-(2-methyl-1,4-benzodioxanyl)]piperazine,
k) 1-[7-(4-fluorobenzofuranyl)]piperazine,
l) 1-[8-(isoquinolyl)]piperazine,
m) 1-[7-(4-bromobenzofuranyl)]piperazine,
n) (+)-1-[5-(2-methoxymethyl-1,4-benzodioxanyl)]piperazine,
o) 1-[7-(4-methylbenzofuranyl)]piperazine,
p) 1-[7-(4-chlorobenzofuranyl)]piperazine,
q) 2-[7-(5-chlorobenzofuranyl)]piperazine, and pharmaceutically acceptable acid addition salts thereof.

7. A compound selected from the group consisting of
a) 1-[5-(1,4-benzodioxanyl)]piperazine,
b) 1-[8-(1,3-benzodioxanyl)]piperazine,
c) 1-[7-(benzofuranyl)]piperazine,
d) 1-[4-(1,3-benzodioxolyl)]piperazine,
e) 1-[5-(2-methoxymethyl-1,4-benzodioxanyl)]piperazine,
f) 1-[7-(5-fluorobenzofuranyl)]piperazine,
g) 1-[8-(1,2,3,4-tetrahydroquinolyl) ]piperazine,
h) 1-[8-(2-oxo-1-benzopyranyl)]piperazine,
i) 1-[8-(2H-1-benzopyranyl)]piperazine,
j) 1-[5-(2-methyl-1,4-benzodioxanyl)]piperazine,
k) 1-[7-(4-fluorobenzofuranyl)]piperazine,
l) 1) 1-[8-(isoquinolyl)]piperazine,
m) 1-[7-(4-bromobenzofuranyl)]piperazine,
n) (+)-1-[5-(2-methoxymethyl-1,4-benzodioxanyl)]piperazine,
o) 1-[7-(4-methylbenzofuranyl)]piperazine,
p) 1-[7-(4-chlorobenzofuranyl)]piperazine,
q) 2-[7-(5-chlorobenzofuranyl)]piperazine, and pharmaceutically acceptable acid addition salts thereof.

* * * * *